US006348614B1

(12) United States Patent
Cohen et al.

(10) Patent No.: US 6,348,614 B1
(45) Date of Patent: Feb. 19, 2002

(54) AMINOBUTYRIC ACID FUNGICIDES

(75) Inventors: Yogal Cohen, Kiryat Ono; Moshe Korat, Meitar, both of (IL)

(73) Assignee: Agrogene Ltd., Kiryat Ono (IL)

( * ) Notice: Subject to any disclaimer, the term of this patent is extended or adjusted under 35 U.S.C. 154(b) by 0 days.

(21) Appl. No.: 09/331,722

(22) PCT Filed: Dec. 24, 1997

(86) PCT No.: PCT/IL97/00423

§ 371 Date: Jun. 25, 1999

§ 102(e) Date: Jun. 25, 1999

(87) PCT Pub. No.: WO98/29387

PCT Pub. Date: Jul. 9, 1998

(30) Foreign Application Priority Data

Dec. 25, 1996 (IL) .................................................. 119908
Dec. 4, 1997 (IL) .................................................. 122435

(51) Int. Cl.$^7$ ........................ C07C 303/00; A01N 37/12
(52) U.S. Cl. ............................. 560/12; 560/38; 560/43; 562/443; 562/450; 564/162; 564/163; 514/538; 514/562; 514/618; 514/619
(58) Field of Search ............................. 560/12, 38, 43; 562/430, 450; 564/162, 163; 514/538, 562, 618, 619

(56) References Cited

U.S. PATENT DOCUMENTS

| | | |
|---|---|---|
| 3,934,036 A | 1/1976 | Irikura |
| 4,070,176 A | 1/1978 | Oshio et al. |

FOREIGN PATENT DOCUMENTS

| | | |
|---|---|---|
| DE | 2513732 | 10/1975 |
| EP | 0718280 | 6/1996 |
| FR | 2287171 | 5/1976 |
| WO | 9308174 | 4/1993 |

OTHER PUBLICATIONS

XP–002070492, Chemical Abstracts, (1996).
XP–002070489, "Synthesis of –Amino–acid peptides. Part 3 Preparation of Racemic and chiral 3–Aminobutyric Acid Derivatives and Peptides Using Dihydro–oxazin–6–ones and Conventional Coupling Reagents", *J. Chem. Soc. Perkin Trans*, pp. 1587–1592, (1982).
XP–002070493, (1973).
Seebach et al., XP–002070487 "Alkylation of –Aminobutanoates with 1.2–induction", pp. 3103, 3106, (1987).
Molander et al., "Reduction of 2–Acylaziridines by Samarium (II) Iodide. An Efficient and Regioselective Route to –Amino Carbonyl Compounds.", *Tetrahedron*, vol. 53, No. 26, pp. 8887–8912, (1997).
Gobeaux et al., "Intramoleculer [2+2] Cycloadition of Keteniminium Salts Derived From –and –amino acids. A Route to Azabicyclic Ketones", *Heterocycles*, vol. 28, No. 1, pp. 29–32, (1985).
Jefford et al., "185. A Practical Synthesis of (2S.3R)–3–Amino–2–methylpentanoic Acid from L–Aspartic Acid" *Helvetica Chimica Acta*, vol. 77, pp. 2142–2146, (1994).
Baldwin et al., "Amino Acid Synthesis via Ring Opening of N–Sulphonyl Aziridine–2–Carboxylate Ester with Organometallic Reagents", *Tetrahedron*, vol. 49, No. 28, pp. 6309–6330, (1993).
Jefford et al., "Enantiospecific Synthesis of Indolizidines 167B and 209D", *Tetrahedron Letters*, vol. 34 No. 19, pp. 3119–3122, (1993).
Saba et al., "Preparation of 1–osyl–2–and 3–pyrrolidinones via ketenes and carbenes", *Heterocycles*, vol. 27 No. 4, pp. 867–870, (1988).
Lim et al., "Regiospecific Reductive Ring Cleavage of N–Substituted Aziridine–2–carboxylates and an Aziridine–2–carboxylates and an Aziridine–2–methanol via Catalytic Hydrogenation Using PD as a Catalyst", *Tetrahedron Letters*, vol. 36, No. 46, pp. 8431–8434, (1995).
Jefford et al., "An Enantiospecific Synthesis of –Amino Acids", *Tetrahedron Letters*, vol. 34, No. 7, pp. 1111–1114, (1993).
XP–002070501, (1969).
XP–002070494, (1998).
Sato et al., "Effect of sample derivatives in liquid chromatographic separations of amine and amino acids enantiomers using diamide–type stationary phases", *Journal of Chromatography*, vol. 666, pp. 463–470, (1994).
Molander et al., "Reduction of 2–Acylaziridines by Samarlum(II) Iodide. An Efficient and Regioselective Route to –Amino Ketones and Esters", *J. Org. Chem.*, vol. 60, pp. 6660–6661, (1995).
Athanasiou et al., "Synthesis of benzenesulfonamide and benzenesilfonohydrazide derivatives. Their effect on Phytopathogenic fungi", *Eur. J. Med Chem.*, vol. 19, No. 3, pp. 281–282, (1984).
Sorensen et al., "Syntheses of Some New Tetrazolylacetic Acids and the Corresponding 3–Substituted Propionic Acids", *Acta Chemica Scandinavica*, vol. 26, pp. 541–548, (1972).
El–Naggar et al., "Synthesis of some 2–Furoyl–, 2–thenoyl–, and 3,4,5–Trimethoxybenzoylamino Acid Derivatives", *Ann. Soc. Chim.*, vol. 50, 2175–2180, (1976).

*Primary Examiner*—Paul J. Killos
(74) *Attorney, Agent, or Firm*—Browdy and Neimark

(57) ABSTRACT

Novel aminobutyric acids derivatives and methods for protecting crops against fungal diseases by applying to the crops or their locus a composition containing an effective amount of said derivatives.

52 Claims, No Drawings

AMINOBUTYRIC ACID FUNGICIDES

CROSS REFERENCE TO RELATED APPLICATION

The present application is the national stage under 35 U.S.C. 371 of PCT/IL97/00423, filed Dec. 24, 1997.

The present invention concerns a novel method to protect plants from pathogenic attack.

BACKGROUND OF THE INVENTION

The use of threo-DL-β-methylaspartic acid and of DL-β-aminobutyric acid for the control of root rot of peas caused by *Aphanomyces euteiches* Drechs, has been described (Papavizas, Plant Disease Reporter, 48, 537–541 (1964), Papavizas, Plant Disease Reporter, 51, 125–129 (1967).

The use of D-alaninie, D-and DL leucine and DL-α-aminobutyric acid at 0.03 M was described to reduce scab in apple caused by *Venturia inaequalis* (Kuc et al., 49: 313–315, 1959).

Van Andel, showed (Tijdschur. Plantenziekten. 64: 307–327, 1958) that DL-serine, D-serine (and to a lesser extent L-serine), phenylserine, DL-threonine but not DL-α aminobutyric acid nor DL-β aminobutyric acid behaved as chemothrerpeutants against the fungus *cladosporium cucumerinum* on cucumber (Ibid. page 318). Oort and Van Andel (1960, Mededel. Landsborowhager school Dpzoekingssta. Staat Gent 25: 981–992) showed that DL-β-aminobutyric acid applied to leaves of tomato protected those leaves against *Phytophthora infestans* (page 987).

Various derivatives of DL-β-aminobutyric acid and β-aminocrotonic acid have been described in the patent literature as fungicides against *Phytophthora infestans* in tomato and *Plasmopara viticola* in grapes (German Patent No. 1,120,802).

Co-pending Israel Patent Application No. 111,824 describes the preparation and use of similar compounds which induce local and systemic resistance of crops against fungal diseases.

OBJECTIVES OF THE INVENTION

It is the objective of the present invention to provide compounds having improved activity against fungi as compared with the compounds of the co-pending Israel patent application 111,824.

SUMMARY OF THE INVENTION

We have found novel compounds of the formula (I):

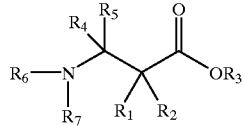

wherein:
$R_1$ and $R_2$ are independently hydrogen, $C_{1-8}$ alkyl, phenyl, and phenyl $C_{1-4}$ alkyl
$R_3$ is $C_{1-23}$ straight or branched or a cyclic alkyl or alkenyl; alkoxyalkyl; halogenated alkyl, phenyl, or benzyl; alkyl phenyl;
$R_4$ and $R_5$ are independently hydrogen or $C_{1-8}$ alkyl;
$R_6$ is hydrogen; $C_{1-8}$ alkyl; $C_{2-8}$ alkanoyl; phenyl $C_{1-4}$ alkyl, benzoyl wherein the phenyl moiety is optionally substituted by one or more halogen atoms or alkyl groups $C_{2-8}$ alkoxycarbonyl; CONHR$_8$ wherein R$_8$ is hydrogen, $C_{1-8}$ alkyl, phenyl, phenyl $C_{1-4}$; phenyl $C_{2-4}$ alkyloxycarbonyl;
$R_7$ is benzenesulfonyl or benzoyl optionally substituted by one or more halogens, alkyl groups, amino groups or alkoxy groups; or thiophene carbonyl;
X is O or NH and salts thereof; and the crop is selected from tomatoes, potatoes, cereals, grapes, melon, wheat and cucumber.

We have also found a novel method of protecting a crop against fungal diseases caused by fungi by applying to the crop or its locus a composition containing an effective amount of a compound of the formula (I).

DETAILED DESCRIPTION OF THE INVENTION

Alkyl as used herein refers to straight chains, branched and cyclic forms and preferably contain one to ten carbon atoms.

$R_1$ and $R_2$ are preferably independently hydrogen, methyl or phenyl, more preferably $R_1$ is hydrogen or methyl and $R_2$ is hydrogen.

$R_3$ is preferably $C_{1-12}$ straight or branched or a cyclic alkyl or alkenyl, phenyl, benzyl, or alkyl phenyl.

$R_4$ and $R_5$ are preferably independently hydrogen or $C_{1-4}$ alkyl, more preferably $R_4$ is hydrogen or methyl and $R_5$ is hydrogen.

$R_6$ is preferably hydrogen, $C_{1-5}$ alkyl; and most preferred hydrogen methyl.

$R_7$ is benzenesulfonyl or benzoyl optionally substituted by one or more halogens, alkyl groups, amino groups or alkoxy groups; or thiophene carbonyl.

Preferred compounds of the invention are:
D,L N-benzenesulfonyl-3-aminobutyranilide;
D,L-N-β-methylbenzoyl-3-aminobutyric acid n-octyl ester;
N-β-methylbenzoyl-3-aminobutyric acid sec butyl ester;
D,L-N-3,4-dichloro benzoyl-3-aminobutyric acid n-octyl ester;
D,L-N-4-chlorobenzoyl-3-aminobutyric acid-2-chloro ethyl ester,
D,L-N-benzensulfonyl-3-amino N-benzyl butyramide;
D,L-N-benzoyl-3-aminobutyric acid 2-chloroethyl ester:
N-β-methylbenzoyl--3-amiobutyric acid 1-methyl-1-pentyl ester;
D,L-N-benzenesulfonyl-3-aminobutyric acid, n-octyl ester;
N-benzenesulfonyl-3-aminobutyric acid-sec-butyl ester;
N-benzenesulfonyl-3-aminobutyric acid-1-methyl-i -butyl ester;
D,L N-4-methoxybenzoyl-3-aminobutyric acid heptyl ester
D,L N-3,5-dimethylbezoyl-3-aminobutyric acid heptyl ester
D,L N-2,6-difluorobenzoyl-3-aminobutyric acid heptyl ester
D,L N-4-tertbutylbenzoyl-3-aminobutyric acid heptyl ester
D,L N-4-methylbenzenesulfonyl-3-aminobutyric acid i-methylpentyl ester
D,L N-benzenesulfonyl-3-aminobutyric acid 3-phenylpropyl ester
D,L N-4-cholrobenzoyl-3-aminobutyric acid 1-methylpentyl ester
D,L N-benzenesulfonyl-3-aminobutyric acid 2-(trichloromethyl)ethyl ester
D,L N-4-methylbenzenesulfonyl-3-aminobutyric 1-methylpropyll ester
D,L N-3,4-dimethylbezoyl-3-aminobutyric acid 1-methylbutyl ester
D,L N-3-methylbezoyl-3-aminobutyric acid heptyl ester
D,L N-3,5-dimethylbezoyl-3-aminobutyric acid 1-methylpentyl D,L N-2,6-dichlorobenzoyl-3-aminobutyric acid heptyl ester
D,L N-2,6-dichlorobenzoyl-3-aminobutyric acid 2-methylpentyl ester
D,L N-4-methylbenzoyl-3-aminobutyric acid 3-phenylpropyl ester
D,L N-3,5-dimethylbezoyl-3-aminobutyric acid 2-chloroethyl ester
D,L N-4-methoxybenzoyl-3-aminobutyric acid 2-chloroethyl ester
D,L N-benzoyl-3-aminobutyric acid 2-(trichloromethyl) ethyl ester
D,L N-4-cholrobenzoyl-3-aminobutyric acid heptyl ester
D,L N-benzenesulfonyl-3-aminobutyric acid 1-methyl-2-methoxyethyl ester
D,L N-2-methylbezoyl-3-aminobutyric acid heptyl ester
D,L N-4-methylbenzenesulfonyl-3-aminobutyric acid 2-bromoethyl ester
D,L N-4-methylbenzenesulfonyl-3-aminobutyric acid heptyl ester
D,L N-4-chlorobenzenesulfonyl-3-aminobutyric acid propyl ester
D,L N-4-methylbenzoyl-3-aminobutyric acid 2-(trichloromethyl)ethyl ester
D,L N-4-methylbenzoyl-3-aminobutyric acid cyclohexyl ester
D,L N-benzoyl-3-aminobutyric acid cyclohexyl ester
D,L N-benzenesulfonyl-3-aminobutyric acid cyclohexyl ester
D,L N-4-chlorobenzenesulfonyl-3-aminobutyric acid heptyl ester
D,L N— benzenesulfonyl-3-aminobutyric acid propyl ester
D,L N-benzoyl-3-aminobutyric acid 2-propenyl ester
D,L N-4-methylbenzoyl-3-aminobutyric acid 1-methylhexyl ester
D,L N-4-methylbenzoyl-3-aminobutyric acid 1-methyldecanyl ester
D,L N-3,4-dimethylbezoyl-3-aminobutyric acid heptyl ester
D,L N-4-methylbezoyl-3-aminobutyric acid 1-methylpentyl ester
D,L N-2-methylaminobenzoyl-3-aminobutyric acid methyl ester.
D,L N-4-chlorobenzensulfonyl-3-aminobutyric acid 1-methylpentyl ester
D,L N-benzensulphonyl-3-aminobutyric acid 3-phenylpropyl ester
D,L N-2-methylaminobenzoyl-3-aminobutyric acid 1-methylpentyl ester
D,L N-benzensulfonyl-3-aminobutyric acid 3,5-dichlorophenyl ester
D,L N-4-2-thiophenebenzoyl-3-aminobutyric acid octyl ester
D,L N-4-2-thiophenebenzoyl-3-aminobutyric acid 1-methylpentyl ester
D,L N-3,4-dimethylbenzoyl-3-aminobutyric acid octyl ester Production methods The novel compounds encompassed by the present application are structurally related to known compounds and can be easily prepared by either derivatising the known compounds or by modifying the procedures for preparing the known compound, as required. These procedures will be apparent to those skilled in the art. The following procedures are illustrative.

Compounds of the formula (I)

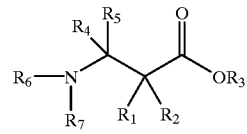

wherein $R_1$ and $R_2$ and $R_4$ are as previously defined and $R_3$ represents hydorgen or $C_{1-8}$ alkyl can be obtained from β-aminobutyric acid.

To prepare compounds of formula (I) where $R_6$ and $R_7$ are as previously defined β-aminobutyric acid is reacted with $NR_7H_2$, wherein $R_7$ is as previously defined. Reactions of this type are described in the literature, e.g., by A. Zilkha and J. Rivilin, J. Org. Chem. 1957, 23, 94.

The present compounds were found to be effective against late blight in potato and tomatoes, powdery mildew in cereals, downy meldow in cucumber, melon and grapes.

The present compounds of this invention will typically be applied to crops or their locus before or after the onset or after the initial signs of fungal attack and may be applied to the foliar surfaces of the crop. The amount of active ingredient to be employed will be sufficient to induce the systemic resistance of the crop to control the fungi and will vary depending on such factors as the species of fungi to be controlled, the type of treatment (for example, spraying dusting, seed treatment, soil drench), the condition of the crop, and the particular active ingredient used.

As an application to the crop or its locus, the compounds will be applied to the crops with a dosage rate of from 0.1 to 5 kg/ha, preferably from 0.2 to 2 kg/ha. with application being repeated as necessary, typically at intervals of every one to three weeks.

Depending on circumstances, the compounds of this invention may be used in association with other pesticides, e.g., fungicides, insecticides, acaricides, herbicides, or plant growth regulating agents in order to enhance their activity or to widen their spectrum of activity.

The compounds of this invention are conveniently employed as fungicidal composition in association with agriculturally acceptable carriers or diluents. Such compositions also form part of the present invention. They may contain, aside from a compound of formula (I) as active agent, other active agents, such as fungicides. They may be employed in either solid or liquid application forms e.g., in the form of a wettable powder, an emulsion concentrate, a water dispersible suspension concentrate ("flowable"), a dusting powder, a granulate, a delayed release form incorporating conventional carriers, diluents and/or adjuvants. Such compositions may be produced in conventional manner, e.g. by mixing the active ingredient with a carrier and other formulating ingredients.

Particular formulations to be applied in spraying forms such as water dispersible concentrates or wettable powders may contain surfactant such as wetting and dispersing agents, e.g., the condensation product of formandehyde with naphthalene sulphonate, an alkyl-aryl-sulphonate, a lignin sulphonate, a fatty alkyl sulphate an ethoxylated alkylphenol and an ethoxylated fatty alcohol.

In general, the formulations include from 0.01 to 90% by weight of active agent, said active agent consisting either of at least one compound of formula (I) or mixture thereof with other active agents, such as fungicides. Concentrated forms of compositions generally contain between about 2 and 80%, preferably between about 5 and 70% by weight of active agent. Application forms of formulation may, for example, contain from 0.01% to 20% by weight, preferably from 0.01% to%5 by weight, of active agent.

Formulation Example I: Wettable powder 50 parts by weight of a compound of formula (I) are ground with 2 parts of lauryl sulphate, 3 parts sodium lignin the sulphonate and 45 parts of finely divided kaolininite until the mean particle size is below 5 microns. The resulting wettable powder so obtained is diluted with water before use to a concentration of between 0.01% to 5% active ingredient. The resulting spray liquor may be applied by foliar spray as well as by root drench application.

Formulation Example II: emulsion concentrate 25 parts by weight of a compound of formula I, 65 parts of xylene, 10 parts of the mixed reaction product of an alkylphenol with xyleneoxide and calcium-dodecyl-benzene sulphonated are thoroughly mixed until a homogeneous solution is obtained. The resulting emulsion concentrate is diluted with water before use.

Formulation Example III: Granulate (for soil treatments)

Onto 94.5 parts by weight of quartz sand in a tumbler mixer is sprayed 0.5 parts by weight of a binder (non-ionic tenside) and is thoroughly mixed. 5 parts by weight of compound of the formula (I) in powdered form are then added and thoroughly mixed to obtain a granulated formulation with a particle size in the range of from about 0.3 to about 0.7 mm. The granulate may be applied by incorporation into the soil adjacent the plants to be tested.

Formulation Example IV: Seed or Tuber Dressing 25 parts by weight of compound of the formula (I), 15 parts of dialkylphenoxy-poly-(ethylenoxy) ethanol, 15 parts of fine silica, 44 parts of fine kaolin, 0.5 parts of a colorant (e.g., crystal violet) and 0.5 pars of xantham gum are mixed and ground a contraplex mill at approximately 10,000 rpm to an average particle size of below 20 micron.

The resulting formulation is applied to the seeds or tubers as an aqueous suspension in an apparatus suitable for that purpose. Where the compound of the formula (I) is liquid, it is first absorbed on the carriers, if desired with the aid of a small amount of a volatile solvent such as acetone. The resulting powder if first allowed to dry if a solvent is used, then the other ingredients are added and the rest of the procedure is carried out.

Formulation Example V: Soil Drench Drip Irrigation 2 parts by weight of compound of the formula (I) are dissolved in 1,000 parts of water. The resulting formulation is applied to plant by drip irrigation.

As previously mentioned, the compounds of formula (I) are effective in activation or enhancing a corp's defense system against fungal diseases caused by fungi. Such activity can be demonstrated in usign the general procedures of the following tests:

while the invention will now be described in connection with certain preferred embodiments in the following examples, it will be understood that it is not intended to limit the invention to these particular embodiments. On the contrary, it is intended to cover all alternatives, modifiations and equivalents as may be included within the scope of the invention as defined by the appended claims. Thus, the following examples, which include preferred embodiments, will serve to illustrate the practice of this invention, it being understood that the particulars shown are by way of example and for purpses of illustrative discussion of preferred embodiments of the present invention only and are presented in the cause of providing what is believed to be the most useful and readily understood description of procedures, as well as of the principles and conceptual aspects of the invention.

EXAMPLES

Example 1

D,L-N-benzenesulfonyl-3-amino N-benzyl butyramide

To 6.0 gr β-Aminobutyric acid in 20 ml water was added 5.4 gr NaOH dissolved in 26 ml water. 10.3 gr Benzenesulfonyl chloride in 36 ml Dichloroethane was added at r.t. during 15 minutes. The mixture was stirred for 10 minutes at r.t. and heated at 68° C. during 4 hr. The phases were separated, and the aqueous one, was acidified with HCl (conc) to pH 2.5. After extrcation with Dichloroethane (DCE) DL-N-benzenesulfonyl-3 aminobutyric acid (I) crystallized from the organic phase. 6.7 gr m.p. 125–127. 4° C.

To 7.7 gr compound I, in 80 ml Dichloroethane, was added 7.5 gr $PCl_5$ in small portions, keeping the mixture temperature at 5° C. The mixture was allowed to warm to r.t. and stirred during 6 hr. Petrol ether 60–80 (400 ml) was added, the chloride was filtered and dried yielding 7.3 gr product (II).

To 3.0 gr of the acid chloride (II) in 30 ml DCE, was added 2.3 gr benzylamine in 5 ml DCE during 10 minutes at 10–15° C. The mixture was heated to 50° C. during 7 hr. 30 ml of water was added, the organic pahse separtated, and after concentration of the solution the product precipitated. 2.66 gr m.p. 105–107° C. NMR and MS spectrocopic methods confirmed the structure.

Example 2

D,L-N-benzensulfonyl-3-aminobutyranilide

To 3.0 gr Acid chloride (II) in 30 ml DCE was added 2.0 gr aniline in 5 ml DCE during 10 minutes at 10–15° C. The mixture was heated at 50° C. during 7 hr. 30 ml of water was added, and the organic phase was separated. Evaportaion of the solvent gave 3.5 gr product. Recrystallization from toluene gave 2.7 gr mp. 130–132° C. NM and MS spectroscopic methods confirmed the structure.

Example 3

D,L-N-β-methyl benzoyl-3-aminobutyric acid n-octyl ester

To 2.0 gr β-Aminobutyric acid in 9 ml water, was added 3.4 gr NaOH in 9 ml water. 3.0 gr of β-Toluoyl chloride in 15 ml DCE was added during 20 minutes at r.t. The mixture was heated at 62° C. during 7 hr. The phases were separated, and the aqueous one was acidified with HCl (conc) to pH 2.0–2.5. The compound precipitated; decantation and recrystallization with water gave after trituration with DCE, 3.3 gr. m.p. 115–118° C., of D,L-β-methylbenzoyl-3-aminobutyric acid (III). to 3.0 gr of the acid (III) in 35 ml DCE, was added 3.2. gr $PCl_5$ in small portions, keeping the mixture temperature at 10–15° C. The mixture was allowed to warm to 25° C. and was stirred for 7 hr. Petrol ether 60–80 (280 ml) was added and oil was separted. Decantation of the solvent and addition of 50 ml Petrol ether gives a crystaline compound. After filtration we obtain 2.5 gr acid chloride IV.

To the chloride IV in 25 ml DCE was added 4.1 gr n-octanol in 5 ml DCE during 20 minutes at 30° C. The mixture was heated at 65° C. during 6 hr. Afte distillation, 25 ml DCE was added, washed with 3×10 ml sodium bicarbonate 2% and dired over $MgSO_4$. Evaporation of the solvent gave 2.1 gr m.p. 41–42° C. of the product. NMR and MS confirmed the structure.

Example 4

N-β-methyl benzoyl-3 aminobutyric acid-sec. butyl ester

Method A

To 2.6 gr chloride IV in 25 ml DCE, was added 2.3 gr 2-butanol in 5 ml DCE, during 10 minutes at 25° C. The mixture was heated at 65° C. during 6 hr. After distillation, 25 ml DCE was added, washed with sodium cicarbonate 2% and dried over $MgSO_4$, Evaporation of the solvent gave 2.2 gr of the product. NM and MS spectroscopic methods confirms the structure.

Method B

The mixture of 2.0 gr D,L-β-methylbenzoyl-3-aminobutyric (III) 0.85 gr 2-butanol, 30 ml Toluene and 0.04 gr $H_2SO_4$ (conc) was heated under reflux for ca 7 hr. The water formed in the reaction was separated by azeotropic distillation. The cooled reaction mixture was washed twice with 15 ml water, sodium bicarbonate 2% and dried over $MgSO_4$. Distillation of the solvent yield 1.7 gr of the ester.

Example 5

D,L-N-3-4-dichlorobenzoyl-3-amino butyric acid n-octyl-ester

D,L-N-3,4-dichlorobenzoyl-3-aminobutyric acid n-octyl ester

To 1.5 gr β-Aminobutyric acid in 5 ml water, was added 2.5 gr NaOH in 6.4. ml water. 3.0 gr of 3,4-dichloro benzoyl chloride in 10 ml DCE was added during 10 minutes at r.t. The mixture was heated at 65° C. during 6.5 hr. The phases were separated. The aqueous phase was washed twice with 15 ml DCE and acidified with HCl (conc) to pH 1.5–2.0. The compound was filtered. 3.1 gr mp 143–146° C. (V) were obtained.

To 2.5 gr compound V in 35 ml dichloroethane (DCE), was added 2.2 gr $PCl_5$ in small portions, keeping the mixture temperature at 10–15° C. The mixture was allowed to warm to 25° C., and stirred for 7 hr. Petrol ether 60–80 was added, the acid chloride precipitated, filtered and dried, yielding 1.5 gr.

To the chloride in 25 ml DCE was added 2.0 gr n-octanol in 5 ml DCE during 10 minutes at 20° C. The mixture was heated at 65° C. during 7 hr. After distillation, 25 ml DCE was added, washed with sodium bicarbonate 2% and dried over $MgSO_4$. Evaporation of the solvent gave 2.0 gr of the titled compound. NMR and MS spectroscopic methods confirmed the sturcture.

Example 6

D,L-N-4-chlorobenzoyl-3-aminobutyric acid 2-chloro-ethyl ester

D,L-N-4-chlorobenzoyl-3-aminobutyric acid-2-chloro-ethyl ester

To 3.0 gr β-Aminobutyric acid in 7 ml water, was added 3.4 gr NaOH in 8.7 ml water. 3.1 gr of β-chlorobenzoyl chloride in 15 ml DCE was added during 15 minutes at 10–15° C. The mixture was heated at 60° C. during 7 hr. The phases were separated, and the aqueous phase was washed twice with 15 ml DCE, and acidified with HCl (conc) to pH 1.5–2.0. The compound was filtered and recristallized with water. 3.94 gr of DL-β-Chlorobenzoyl-3 aminobutyric acid (VI) was obtained.

To 3.0 gr of acid VI in 25 ml Dce, was added 2.93 gr PCl in small portions, keeping the mixture temperature at 8–10° C. The mixture was allowed to warm to 25–27° C. and stirred for 7 hr. Petrol ether 60–80 (150 ml) was added, the chloride was filtered and dried yielding 2.7 gr (VII).

To 2.5 gr of acid chloride VII in 20 ml DCE was added 2-chloroethanol in 5.0 ml DCE during 10 minutes at 15–17° C. The mixture was heated at 65° C. during 7 hr. After distillation 35 ml DCE was added, and washed with sodium bicarbonate 2%. Evaporation of the solvent gave 1.73 gr product. Crystallization from cyclohexane yield 0.5 gr. mp 80–81° C. NMR and MS spectroscopic methods confirmed the sturcture.

Example 7

DL-N-benzenesulfonyl-3-aminobutyric acid n-octyl ester
DL-N-benzenesulfonyl-3-aminobutyric acid n-octyl ester The mixture of 2.0 gr DL-N benzensulfonyl-3 aminobutyric acid (I), 1.78 gr n-octanol, 30 ml Toluene and 0.04 gr $H_2SO_4$ (conc) was heated under refulux for ca 3 hr. The water formed in the reaction was separated by azeotropic distillation. The cooled reaction mixture was washed twice with bicarbonate 2%, and dried over magnesium sulfate. Distillation of the solvent and alcohol yield 2.0 gr product, confirmed by spectroscopy.

Example 8

N-benzenesulfonyl-3-aminobutyric acid-sec butyl ester
N-benzenesulfonyl-3-aminobutyric acid-sec butyl ester The mixture of 2.0 gr DL-N benzensulfonyl-3 aminobutyric acid (I), 1.0 gr 2-butanol, 30 ml toluene and 0.04 gr $H_2SO_4$ (conc) was heated under reflux for ca 6 hr. The water formed in the reaction was separated by azeotropic distillation. The cooled reaction mixture was washed twice with bicarbonate 2%, and dried over magnesium sulfate. Distillation of the solvent and alcohol yield 1.8 gr procuct, confirmed by spectroscopy.

Example 9

N-benzenesulfonyl-3-aminobutyric acid 1-methyl-1-butyl ester
N-benzenesulfonyl-3-aminobutyric acid 1-methyl-1-butyl ester The mixture of 2.0 gr DL-N benzensulfonyl-3 aminobutyric acid (I), 1.2 gr 2-Pentanol, 30 ml toluene and 0.04 gr $H_2SO_4$ (conc) was heated under reflux for ca 6 hr. The reaction was treated as in the previous example. 2.0 gr of the ester was obtained, confirmed by spectroscopy.

Example 10

N-β-methylbenzoyl-1-aminobutyric acid-1-methyl-1-pentyl ester
N-β-methylbenzoyl-1-aminobutyric acid-1-methyl-1-pentyl ester The mixture of 2.0 gr DL-p methylbenzoyl-3 aminobutyric acid (III), 1.6 gr 2-hexanol, 30 ml toluene and 0.04 gr $H_2SO_4$ (conc) was heated under reflux for ca 7 hr. The water formed in the reaction was separated by azeotropic distillation. The cooled reaction mixture was washed with 3×15 ml water, 2×15 ml bicarbonate 2% and dried over $MgSO_4$. After distillation of solvent and alcohol 2.2 gr of the ester was obtained, confirmed by spectorscopy.

Example 11

DL-N-benzoyl-3-aminobutyric acid 2-chloroethyl ester
DL-N-benzoyl-3-aminobutyric acid 2-chloroethyl ester To 1.68 gr DL-N-benzoyl-3-aminobutyric acid chloride, prepared in an analogous way as the acid chloride VII (Example 6), in 25 ml DCE was added 2.5 gr 2-chloroethanol in 5 ml DCE during 10 minutes, at 19–20° C. The mixture was heated at 65–67° C. for ca 7 hr. After distillation of the solvent and alcohol, 20 ml of DCE was added, an washed with 2% bicarbonate. Evaporation of the solvent yield 1.4 gr product, confirmed by spectroscopy.

Example 12

N-benzenesulfonyl-3-aminobutyric acid-1 methyl 2-methoxy ethyl ester.

To 6.0 gr of β-Aminobutyric acid in 20 ml water, was added 5.4 gr of NaOH dissolved in 26 ml water. 10.3 gr of benzensulfonyl chloride in 36 ml dichloroethane was added at r.t. during 15 minutes. The mixture was stirred 10 minutes at r.t. and heated at 68° C. during 4 hr. The phases were separated, and the aqueous one, was acidified with HCl (conc) to pH 2.5. After the extraction with dichloroethane, n-benzenesulfonyl-3-aminobutyric acid crystallized from the organic phase. 6.7 gr m.p. 125–127.4° C. to 7.7 gr of n-benzenesulfonyl-3-aminobutyric acid in 80 ml DCE, was added 7.5 gr in small portions, keeping the mixture temperatured at 5° C. The mixture was allowed to warm to r.t.

and stirred during 6 hr. Petrol ether 60–80 (400 ml) was added, the chloride was filter and dried yielding 7.3 gr of the acid chloride. The 2.0 gr of the acid chloride in 30 ml DCE was added 1-methoxy-2-propanol dissolved in 5 ml DCE at 10–15° C. The mixture was heated at 63–65° C. during 6.5 hr. The reaction was washed twice with 20 ml water and sodium bicarbonate 2% and dried over $MgSO_4$ and Distillation of the solvent and excess alcohol yield 1.75% of the product. The structure was confirmed by MS and NMR spectroscopic methods. By proceeding as described above, using the suitable starting materials compounds 19,29,31,36 and 47 were prepared.

Example 13
N-2-methylaminobenzoyl-3-aminobutyric acid methyl ester.

The mixture of 17.7 gr N-methylisatoic anhydride, 10.3 gr β-Aminobutyric acid, 1.5 gr triethylamine and 150 n Toluene, was refluxed during 7 hr. The solids were removed by filtration and N-2-methylaminobenzoyl-3-aminobutyric acid crystallized from the filtrate. The compound was filtered and washed with water and toluene where 5.4 gr were obtained. To 2.0 gr of N-2-methylaminobenzoyl-3-aminobutyric acid in 19 gr methanol, 2,3 gr of thionyl chloride was added at r.t. The mixture was heated to 60° C. during 6.5 hr. After the distillation of methanol, 50 ml Dichloroethane was added. The solution was washed twice with 25 ml sodium bicarbonate 2%, 25 ml water and dried over $MgSO_4$. After the evaporation of the solvent, 1.8 gr product was obtained. NMR and MS spectroscopic methods confirmed the structure.

Example 14
N-4-methoxy-benzoyl-3-aminobutyric acid n-heptyl ester.

To 9.2 gr β-aminobutyric acid in 32 ml water, was added 15.6 gr of NaON in 40 ml water. 16.6 gr of 4-methoxybenzoylchloride in 60 ml Dichloroethane (DCE) was added during 20 minutes at 15–20° C. The mixture was heated at 65° C. during 7.5 hr. The phases were separated, and the aqueous one was acidified with HCl (conc) to pH 2–2.5. The compound precipitated. 18.7 gr of n-4-methoxy-benzoyl-3-aminobutyric acid was obtained m.p. 112–116 after recrystallization with DCE. The mixture of 2.0 gr n4-methoxy-benzoyl-3-aminobutyric acid, 1.6 gr 1-heptanol, 30 ml Toluene and 0.04 gr $H_2SO_4$(conc) was heated under reflux for 7 hr. The water formed in the reaction was separated by a zeotropic distillation. The cooled reaction was washed twice with 25 ml water. After the evaporation of the solvent, the excess alcohol was distilled at 90° C. (0.4 mm Hg) and 0.8 gr product was obtained. NMR and MS spectroscopic methods confirmed the sturcture.

Example 15
N-benzoyl-aminobutyric acid-cyclohexyl ester.

The mixture of 2.0 gr n-benzoyl-3-aminobutyric acid, 1.6 gr cyclohexanol, 30 ml toluene and 0.04 gr $H_2SO_4$ (conc) was heated under reflux during 2 hr, the water formed in the reaction was separated by azeotropic distillation. The cooled solution was washed with water and twice with 30 ml 2% sodium bicarbonate. After the evaporation of the solvent, and distillation of the excess alcohol at 50° C., 0.4 mmHg, 1.5% oily product, which soldified, was obtained. m.p. 60–63° C. The sturcture was confirmed by MS and NMR spectoroscopic methods.

Example 16
N-benzoyl-3-aminobutyric acid-2 propenyl ester (compound 42)

The mixture of 10 gr n-benzoyl-3-aminobutyric acid 4.8 gr allylalcohol, 70 ml toluene and 0.2 gr $H_2SO_4$ (conc) was heated under reflux during 7 hr. The water formed in the reaction was separated by azeotropic distillation. The solution was washed with water, 2% sodium bicarbonate and dried over $MgSO_4$ After the distillation of the solvent 5.0% of the product was obtained. MS and NMR spectroscopic methods approved the sturcture.

Compounds 12–18, 20–28, 30–35,37–46 and 48 were prepared by similar manners to those described in examples 13–16 using suitable starting materials.

I. Activity against late blight in potato and tomato.

For the following experiments we have used six weeks old potted potato plants (*Solanum tuberosum* cultivar Alpha) or 4-weeks old potted tomato plants (Lycopersicon esculentum cultivar Florida basket). Plants were sprayed with the test compound and two days later were challenge inoculatedd with the lated blight fungus *Phytophthora infestans*. Inoculation was carried out as follows:

1. The fungus was grown on potato tuber slices at 15° C. for 7 days.
2. Sporaganic produced on tuber slices were harvested into cold (4° C.) distilled water and their concentration adjusted to $2.5-3 \times 10^3$ sporaganic/ml.
3. Sporangical suspension was sprayed to run off onto the treated plants. Untreated plants were also inoculated as controls.
4. Inoculated plants were placed in a dew chamber at 18° C. for 20 hr and then transferred into a growth chamber at 20° C. with 12 hr lighr photoperiod and 60–70% RH.
5. At 4–7 days post inoculation the intensity of disease developed was visually activated by assessing the percentage of the foliage area killed by the fungus.
6. Control efficacy achieved by the spray treatment was calculated relative to the disease intensity seen on the control plants. For example when % foliage area killed was 90% in the control plants and 10% in the treated plants, control efficancy was calculated as $$\left(1 - \frac{10}{90}\right) \cdot 100 = 88.0\%$$

Results are shown in Tables 1 and 2.

TABLE 1

Activity of some BABA Derivatives against late blight caused by Phytophthora infestans in potato and tomato.
Control Efficacy %

| Compounds from | Potato 26.7.96 (ppm) | | 17.7.096 (ppm) | | 14.8.96 (ppm) | Tomato 12.7.96 (ppm) | | 14.8/96 (ppm) |
| --- | --- | --- | --- | --- | --- | --- | --- | --- |
| | 500 | 2000 | 500 | 2000 | 2000 | 500 | 2000 | 2000 |
| Example 1 | 49 | 79 | 57 | 77 | 72 | 82 | 97 | 90 |
| Example 2 | 42 | 68 | 45 | 81 | 74 | 85 | 85 | 83 |
| Example 6 | — | — | 75 | 50 | 88 | 76 | 79 | 67 |
| Example 3 | 85 | 92 | 70 | 81 | 88 | — | 70 | 93 |
| Example 4 | 23 | 42 | 56 | 75 | 77 | — | 85 | 90 |

TABLE 2

Activity of some BABA derivatives against late blight cause by Phytophthora infestans in potato, 3-8 days after inoculation.
Dose: 2000 ppm
Control efficacy %

| Compounds from | 3 days | 4 days | 6 days | 8 days |
| --- | --- | --- | --- | --- |
| Example 7 | 100 | 100 | 82 | 77 |
| Example 8 | 100 | 92 | 87 | 50 |

TABLE 2-continued

Activity of some BABA derivatives against late blight cause by
Phytophthora infestans in potato, 3-8 days after inoculation.
Dose: 2000 ppm
Control efficacy %

| Compounds from | 3 days | 4 days | 6 days | 8 days |
|---|---|---|---|---|
| Example 9 | 99 | 97 | 82 | 62 |
| Example 10 | 100 | 100 | 97 | 87 |
| Example 11 | 95 | 92 | 82 | 70 |

Experimental

Late blight in potato caused by *Phytophthora infestans*, additional examples

Potato plants (cv.Alpha) were raised from tubers in 1 liter pots in the greenhouse. At 4 weeks after "sowing" when had 3–4 shoots with 10–12 leaves, plants were sprayed with test solutions onto their adaxial surfaces and incubated at 20° C. growth cabinets. Two days after spray plants were inoculated with sporangial suspension (2000 sporangia/ml) of *P.infestans* (A2 mating type, resistant to metalaxyl). Inoculated plants were placed in 100% relative humidity in the dark for 20 hours and then returned to a 20° C. growth cabined for symptom production. Percentage leaf area covered with blight symptoms was visually assessed 6 days after inoculation. Control efficacy was calculated relative to the control inoculated plants. The results are shown in Table 3.

TABLE 3

Activity of some additional BABA derivatives against late blight caused
by Pytophtora infestans in Potato 6 days after inoculation.
Dose: 500 ppm
$CH_3C(H)NHR_7CH_2C(O)$—$OR_3$

| Compd. | $R_7$ | $R_3$ | Control efficacy (%) 6d |
|---|---|---|---|
| 12 | 4-$CH_3OC_6H_4CO$ | $(CH_2)_6CH_3$ | 89 |
| 13 | 6,5-$(CH_6)_2C_6H_6CO$ | $(CH_2)_6CH_3$ | 84 |
| 48 | 2-$C_4H_3SCO$ | $(CH2)7CH3$ | 82 |
| 14 | 2,6-$F_2C_6H_6CO$ | $(CH_2)_6CH_3$ | 79 |
| 15 | 4-$C(CH_6)_6C_6H_4CO$ | $(CH_2)_6CH_3$ | 79 |
| 16 | 4-$CH_6C_6H_4SO_2$ | $CH(CH_6)(CH_2)_3CH_3$ | 79 |
| 50 | 4-$ClC_6H_5SO_2$ | $CH(CH_3)(CH_2)_3CH_3$ | 77 |
| 17 | $C_6H_5SO_2$ | $(CH_2)_3C_6H_5$ | 76 |
| 18 | 4-$ClC_6H_4CO$ | $CH(CH_3)(CH_2)_3CH_3$ | 76 |
| 51 | $C_6H_5SO_2$ | $(CH_2)_3C6H5$ | 76 |
| 49 | 2-$C_4H_3SCO$ | $CH(CH_3)(CH_2)_3CH_3$ | 75 |
| 19 | $C_6H_5SO_2$ | $CH_2CCl_3$ | 75 |
| 20 | 4-$CH_6C_6H_4SO_2$ | $CH(CH_3)CH_2CH_3$ | 75 |
| 52 | 2-$CH_3NHC_6H_4CO$ | $CH(CH_3)(CH_2)_3CH_3$ | 74 |
| 21 | 3,4di$CH_6C_6H_6CO$ | $CH(CH_3)(CH_2)_2CH_3$ | 73 |
| 22 | 3-$CH_6C_6H_4CO$ | $(CH_2)_6CH_3$ | 70 |

Late blight in tomato caused by *Phytophthora infestans*

Tomato plants (cv.baby) were raised from seed in 0.2 liter pots in the greenhouse. At 3 weeks after sowing when had 6 leaves plants were sprayed with the test solution onto their adaxial surfaces. They were inoculated and further handled and assessed for disease development as described in Section 1 above. The results are shown in Table 4.

TABLE 4

Activity of some BABA derivatives against late blight caused
by Pytophtora infestans in Tomato, 7 days after inoculation.
Dose: 500 ppm
$CH_3C(H)NHR_7CH_2C(O)$—$OR_3$

| Compd. | $R_7$ | $R_3$ | Control efficacy % 7d |
|---|---|---|---|
| 35 | $ClC_6H_5SO_2$ | $CH_2CH_2CH_3$ | 81 |
| 36 | 4-$CH_3C_6H_4CO$ | $CH_2CCl_3$ | 81 |
| 37 | 4-$CH_3C_6H_4CO$ | cyclohexyl | 78 |
| 38 | $C_6H_5CO$ | cyclohexyl | 78 |
| 39 | $C_6H_5SO_2$ | cyclohexyl | 75 |
| 52 | 2-$CH_3NHC_6H_4CO$ | $CH(CH_3)(CH_2)_3CH_3$ | 75 |

II. Activity against powdery mildew in cereals

For the following experiments we have used 10-days old potted wheat plants (*Triticum asetivum* cultivar Atir) and barley plants (*Hhordeum vulgaris* cultivar Amidon).

Plants were sprayed with the test compounds and two days lated were inoculated with the powdery mildew fungal pathogens. Wheat was inoculated with *Erysiphe granims tritici*. Barley was inoculated with the powdery *Erysiphe granims hordei*.

Inoculation was done by shaking infected donor plants harboring abundant conidia over the treated plants. Untreated plants were also inoculated as controls. Inoculated plants were placed in a growth chamber at 20–22C with 1 rhr photoperioed and 50–60% RH. At 9–10 days after inoculation disease intesity was visually assessed by estimating the percentage leaf area occupied by fungal colonies.

Control efficacy of the disease achieved by the sprayed test compound was calculated relative to the amount of disease seen in the control. For example when% foliage area occupied by fungal colonies was 90% treated plants, control efficacy was calculated as $$\left(1 - \frac{10}{90}\right) \cdot 100 = 88.9\%$$

Results are shown in Table 5

TABLE 5

Activity of some BABA derivatives against powdery mildew caused by
Erysiphe graminis in cereals.
Control Efficacy %

| | Barley 17.9.96 | | Wheat 7.8.96 | |
|---|---|---|---|---|
| Compound from | 500 | 2000 | 500 | 2000 |
| Example 1 | 25 | 75 | — | — |
| Example 6 | 62 | 75 | — | — |
| Example 4 | 87 | 95 | 96 | 96 |
| Example 5 | 82 | 85 | 76 | 92 |

Powdery mildew in wheat caused by *Erysiphe grarinis tritici*, additional examples.

Wheat plants (cv.Shafir) were raised from seed in the greenhouse, 30 plants per 0.2 liter pot. When the first leaf was fully developed plants were sprayed with the test solutions and placed in a 20° C. growth cabinet. Two days after spraying plants were dusted with conidia of *E. graminis tritict* so that about 100 spores were settled on 1 cm² of leaf area (both surfaces). Inoculated plants were placed in a 20° C. growth cabinet for 7 days until number of fungal colonies per plant were counted. Control efficacy was calculated relative to number of colonies developed on the control-inoculated untreated plants. The results are shown in Table 6.

TABLE 6

Activity of some BABA derivatives against powdery mildew caused by Erysiphe graminis in wheat 7 days after inoculation.
Dose: 500 ppm
$CH_3C(H)NHR_7CH_2C(O)—OR_3$

| Compd. | $R_7$ | $R_3$ | Control efficacy (%) 7d |
|---|---|---|---|
| 38 | $C_6H_5CO$ | Cyclohexyl | 100 |
| 53 | $C_6H_5SO_2$ | $3,5\text{-}(Cl)_2C_6H_3$ | 100 |
| 50 | $4\text{-}ClC_6H_4SO_2$ | $CH(CH_3)(CH_2)_3CH_3$ | 92 |
| 12 | $4\text{-}CH_3OC_6H_4CO$ | $(CH_2)_6CH_3$ | 85 |
| 32 | $2\text{-}CH_3C_6H_4CO$ | $(CH_2)_6CH_3$ | 83 |
| 16 | $4\text{-}CH_3C_6H_4SO_2$ | $CH(CH_3)(CH_2)_3CH_3$ | 83 |
| 35 | $4\text{-}ClC_6H_5SO_2$ | $CH_2CH_2CH_3$ | 81 |
| 47 | $2\text{-}CH_3NHC_6H_4CO$ | $CH_3$ | 81 |
| 41 | $C_6H_5SO_2$ | $CH_2CH_2CH_3$ | 77 |
| 42 | $C_6H_5CO$ | $CH_2CH=CH_2$ | 77 |
| 43 | $4\text{-}CH_3C_6H_4CO$ | $CH(CH_3)(CH_2)_4CH_3$ | 75 |
| 44 | $4\text{-}CH_3C_6H_4CO$ | $CH(CH_3)(CH_2)_5CH_3$ | 74 |
| 15 | $4\text{-}C(CH_3)_3C_6H_4CO$ | $(CH_2)_6CH_3$ | 74 |
| 13 | $3,5\text{-}C(CH_3)_2C_6H_5CO$ | $(CH_2)_6CH_3$ | 72 |
| 45 | $3,4\ diCH_3C_6H_3CO$ | $(CH_2)_6CH_3$ | 71 |
| 46 | $4\text{-}CH_3C_6H_4CO$ | $CH(CH_3)(CH_2)_3CH_3$ | 69 |
| 54 | $3,4\text{-}(CH_3)_2C_6H_3CO$ | $(CH_2)_7CH_3$ | 69 |

III. Downy mildew in cumber and melon caused by *Pseudoperonospora cubensis*

Cucumber plants (cv,Dlila) and melon plants (cv.Ein Dor) were raised from seeds in 0.2 liter pots in the greenhouse. At 3 weeks after sowing when had 3 true leaves they were inoculated with sporangial suspension (1000 sporangia/ml) of *P.cubensis* (resistant to metalaxyl) and placed in 100% relative humidity in the dark for 20 hr. They were then place in a 20° C. growth cabinet for 7 days and assessed for disease development. Percentage leaf area covered with disease symptoms was evaluated and control efficacy was calculated relative to control inoculated plants. The results are shown in Tables 7 and 8.

TABLE 7

Activity of some BABA derivatives against downy mildew caused by Pseudoperonospora cubesis in melon, 7 days after inoculation.
Dose: 500 ppm
$CH_3C(H)NHR_7CH_2C(O)—OR_3$

| Compd. | $R_7$ | $R_3$ | Control efficacy % 7 days |
|---|---|---|---|
| 12 | $4\text{-}CH_3OC_6H_4CO$ | $(CH_2)_6CH_3$ | 100 |
| 15 | $4\text{-}C(CH_3)_3C_6H_4CO$ | $(CH_2)_6CH_3$ | 97 |
| 17 | $C_6H_5SO_2$ | $(CH_2)_3C_6H_5$ | 87 |
| 18 | $4\text{-}ClC_6H_4CO$ | $CH(CH_3)(CH_2)_3CH_3$ | 87 |
| 51 | $C_6H_5SO_2$ | $(CH_2)_3C_6H_5$ | 87 |
| 22 | $3\text{-}CH_3C_6H_4CO$ | $(CH_2)_6CH_3$ | 83 |
| 19 | $C_6H_5SO_2$ | $CH_2CCl_3$ | 83 |
| 25 | $3,4Cl_2C_6H_3CO$ | $CH(CH_3)(CH_2)_3CH_3$ | 80 |
| 32 | $2\text{-}CH_3C_6H_4CO$ | $(CH_2)_6CH_3$ | 77 |
| 33 | $4\text{-}CH_3C_6H_4SO$ | $CH_2CH_2Br$ | 75 |
| 27 | $3,5\text{-}(CH_3)_2C_6H_3CO$ | $CH_2CH_2Cl$ | 73 |
| 23 | $3,5\text{-}(CH_3)_2C_6H_3CO$ | $CH(CH_3)(CH_2)_3CH_3$ | 73 |
| 34 | $4\text{-}CH_3C_6H_4SO_2$ | $(CH_2)_6CH_3$ | 70 |
| 29 | $C_6H_5CO$ | $CH_2CCl_3$ | 70 |

TABLE 8

Activity of some BABA derivatives against dony mildew caused by Pseudoperonospora cubesis in cucumber, 7 days after inoculation.
Dose: 500 ppm
$CH_3C(H)NHR_7CH_2C(O)—OR_3$

| Compd. | $R_7$ | $R_3$ | Control efficacy (%) 7d |
|---|---|---|---|
| 52 | $2\text{-}CH_3NHC_6H_4CO$ | $CH(CH_3)(CH_2)_3CH_3$ | 97 |
| 40 | $ClC_6H_5SO_2$ | $(CH_2)_6CH_3$ | 82 |
| 36 | $4\text{-}CH_3C_6H_4CO$ | $CH_2CCl_3$ | 82 |
| 38 | $C_6H_5CO$ | Cyclohexyl | 80 |
| 35 | $ClC_6H_5SO_2$ | $CH_2CH_2CH_3$ | 77 |
| 37 | $4\text{-}CH_3C_6H_4CO$ | Cyclohexyl | 75 |
| 39 | $C_6H_5SO_2$ | Cyclohexyl | 70 |

IV. Downy mildew in grapes caused by Plasmoparavlticola

Grape plants (cv.Superior) were raised from cuttings and when developed 5–6 expanded leaves they were sprayed with the test solutions on their abaxial (lower) leaf surfaces. Two days after spraying plants were inoculated with sporangial suspension of *P.viticola* (104 sporangia/ml) onto their lower leaf surface and placed in 100% relative humidity for 20 hr. The plants were then placed in a growth cabinets 20° C. for 10 days. Disease development was assessed according to the abaxial leaf surfaces area covered with fungal sporulation. Fungal sporulation was induced by placing the infected plants in 100% relative humidity in the dark for 48 hr. The results are shown in Table 9.

TABLE 9

Activity of some BABA derivatives against downy mildew caused by Peronospora viticola in Grapes, 10 days after inoculation.
Dose: 500 ppm
$CH_3C(H)NHR_7CH_2C(O)—OR_3$

| Compd. | $R_7$ | $R_3$ | Control efficacy % 10d |
|---|---|---|---|
| 16 | $4\text{-}CH_3C_6H_4SO_2$ | $CH(CH_3)(CH_2)_3CH_3$ | 100 |
| 14 | $2,6\text{-}F_2C_6H_3CO$ | $(CH_2)_6CH_3$ | 100 |
| 23 | $3,5\text{-}(CH_3)_2C_6H_3CO$ | $CH(CH_3)(CH_2)_3CH_3$ | 100 |
| 20 | $4\text{-}CH_3C_6H_4SO_2$ | $CH(CH_3)CH_2CH_3$ | 100 |
| 24 | $3,4Cl_2C_6H_3CO$ | $(CH_2)_6CH_3$ | 100 |
| 25 | $3,4Cl_2C_6H_3CO$ | $CH(CH_3)(CH_2)_3CH_3$ | 100 |
| 26 | $4\text{-}CH_3C_6H_4CO$ | $(CH_2)_3C_6H_5$ | 99 |
| 15 | $4\text{-}C(CH_3)_3C_6H_4CO$ | $(CH_2)_6CH_3$ | 97 |
| 27 | $3,5\text{-}(CH_3)_2C_6H_3CO$ | $CH_2CH_2Cl$ | 97 |
| 17 | $C_6H_5SO_2$ | $(CH_2)_3C_6H_5$ | 97 |
| 51 | $C_6H_5SO_2$ | $(CH_2)_3C_6H_5$ | 97 |
| 19 | $C_6H_5SO_2$ | $CH_2CCl_3$ | 94 |
| 28 | $4\text{-}CH_3OC_6H_4CO$ | $CH_2CH_2Cl$ | 91 |
| 29 | $C_6H_5CO$ | $CH_2CCl_3$ | 91 |
| 30 | $4\text{-}ClC_6H_4CO$ | $(CH_2)_6CH_3)$ | 91 |
| 18 | $4\text{-}ClC_6H_4CO$ | $CH(CH_3)(CH_2)_3CH_3$ | 91 |
| 31 | $C_6H_5SO_2$ | $CH(CH_3)CH_2OCH_3$ | 82 |

What is claimed:
1. A compound having the formula (I)

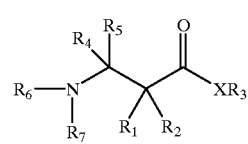

Wherein:
a) $R_1$ and $R_2$ are independently hydrogen, $C_{1-8}$ alkyl, phenyl, and phenyl $C_{1-4}$ alkyl
b) $R_3$ is $C_{1-23}$ straight or branched or a cyclic alkyl or alkenyl; alkoxyalkyl halogenated alkyl, phenyl, or benzyl; alkyl phenyl;
c) $R_4$ and $R_5$ are hydrogen or $C_{1-8}$ alkyl where at least one of $R_4$ and $R_5$ is $C_{1-8}$ alkyl;
d) $R_6$ is hydrogen; $C_{1-8}$ alkyl; $C_{2-8}$ alkanoyl; phenyl $C_{1-4}$ alkyl, benzoyl wherein the phenyl moiety is optionally substituted by one or more halogen atoms or alkyl groups $C_{2-8}$ alkoxycarbonyl; $CONHR_8$ wherein $R_8$ is hydrogen, $C_{1-8}$ alkyl, phenyl, phenyl $C_{1-4}$ alkyl; phenyl $C_{2-4}$ alkoxycarbonyl;
e) $R_7$ is benzenesulfonyl or benzoyl optionally substituted by one or more halogens, alkyl groups, amino groups or alkoxy groups; or thiophene carbonyl;
f) X is O or NH; and
salts thereof; with the proviso that when X is oxygen, $R_1$ is hydrogen and $R_2$ is ethyl, then $R_3$ is neither methyl nor ethyl; and when X is oxygen, $R_2$ is hydrogen and $R_3$ is methyl, then $R_1$ is not ethyl.

2. A compound according to claim 1, wherein $R_1$ and $R_2$ are independently hydrogen, $R_3$ is $C_{1-23}$ straight or branched or a cyclic alkyl or alkenyl; alkoxyalkyli halogenated alkyl, phenyl, or benzyl; alkyl phenyl; $R_4$ and $R_5$ are independently hydrogen or $C_{1-3}$ alkyl; $R_6$ is hydrogen: $R_7$ is benzenesulfonyl or benzoyl optionally substituted by one or more halogens, alkyl groups, amino groups or alkoxy groups; or thiophene carbonyl; and X is oxygen or —NH.

3. A compound according to claim 1, wherein $R_1$, $R_2$, $R_5$, and $R_6$ are hydrogen: $R_3$ is $C_{1-23}$ straight or branched or a cyclic alkyl or alkenyl; alkoxyalkyli halogenated alkyl, phenyl, or benzyl; alkyl phenyl, or benzyl: $R_4$ is methyl: and $R_7$ is benzenesulfonyl; or benzoyl optionally substituted by one or more halogens, alkyl groups, amino groups or alkoxy groups; or thiophene carbonyl; and X is oxygen or NH.

4. A method for protecting a crop against fungal diseases comprising applying to the crop or its locus a composition containing an effective amount of a compound having the formula

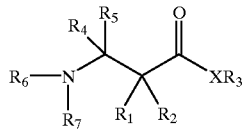

wherein:
a) $R_1$ and $R_2$ are independently hydrogen, $C_{1-8}$ alkyl, phenyl, and phenyl $C_{1-4}$ alkyl;
b) $R_3$ is $C_{1-23}$ straight or branched or a cyclic alkyl or alkenyl; alkoxyalkyli halogenated alkyl, phenyl, or benzyl; alkyl phenyl;
c) $R_4$ and $R_5$ are independently hydrogen or $C_{1-8}$ alkyl;
d) $R_6$ is hydrogen: $C_{1-8}$ alkyl; $C_{2-3}$ alkanoyl; phenyl $C_{1-4}$ alkyl, benzoyl wherein the phenyl moiety is optionally substatuted by one or more halogen atoms or alkyl groups, $C_{2-8}$ alkoxycarbonyl; $CONHR_8$ wherein $R_8$ is hydrogen, $C_{1-3}$ alkyl, phenyl, phenyl $C_{1-4}$ alkyl; phenyl $C_{2-4}$ alkyloxycarbonyl;
e) $R_7$ is benzenesulfonyl or benzoyl optionally substituted by one or more halogens, alkyl groups, amino groups or alkoxy groups; or thiophene carbonyl;
f) X is O, or NH, and salts thereof.

5. A method according to claim 4 wherein $R_1$ and $R_2$ are independently hydrogen, $R_3$ is $C_{1-23}$ straight or branched or a cyclic alkyl or alkenyl; alkoxyalkyli halogenated alkyl, phenyl, or benzyl; alkyl phenyl; optionally substituted by halogen; phenyl or benzyl, $R_4$ and $R_5$ are independently hydrogen or $C_{1-3}$ alkyl; $R_6$ is hydrogen; $R_7$ is benzenesulfonyl or benzoyl optionally substituted by one or more halogens, alkyl groups, amino groups or alkoxy groups; or thiophene carbonyl; and X is oxygen or —NH.

6. A method according to claim 4, wherein $R_1$, $R_2$, $R_5$, and $R_6$ are hydrogen: $R_3$ is $C_{1-23}$ straight or branched or a cyclic alkyl or alkenyl; alkoxyalkyli halogenated alkyl, phenyl, or benzyl; $R_4$ is methyl; and $R_7$ is benzenesulfonyl or benzoyl optionally substituted by one or more halogens, alkyl groups, amino groups or alkoxy groups; or thiophene carbonyl; and X is oxygen or NH.

7. A method according to claim 4 wherein the compound is applied to the crop at a dosage rated of from 0.1 to 5 kg/ha.

8. A method according to claim 4 wherein the compound is applied to the crop at a dosage rate of 0.2 to 2 kg/ha.

9. A method of protecting tomatoes or potatoes against Early Bight or Late Blight comprising of applying to the tomato or potato plant or its locus an effective amount of the compound having the formula (I)

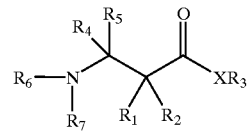

Wherein:
a) $R_1$ and $R_2$ are independently hydrogen, $C_{1-8}$ phenyl, and phenyl $C_{1-4}$ alkyl
b) $R_3$ is $C_{1-23}$ straight or branched or a cyclic alkyl or alkenyl; alkoxyalkyli halogenated alkyl, phenyl, or benzyl; alkyl phenyl;
c) $R_4$ and $R_5$ are independently hydrogen or $C_{1-8}$ alkyl;
d) $R_6$ is hydrogen; $C_{1-8}$ alkyl; $C_{2-8}$ alkanoyl; phenyl $C_{1-4}$, alkyl, benzoyl wherein the phenyl moiety is optionally substatuted by one or more halogen atoms or alkyl groups, $C_{2-8}$ alkoxycarbonyl; $CONHR_8$ wherein $R_8$ is hydrogen, $C_{1-8}$ alkyl, phenyl, phenyl $C_{1-4}$ alkyl; phenyl $C_{1-4}$ alkyloxycarbonyl;
e) $R_7$ is benzenesulfonyl or benzoyl optionally substituted by one or more halogens, alkyl groups, amino groups or alkoxy groups; or thiophene carbonyl;
f) X is O, or NH, and salts thereof.

10. A method according to claim 9, wherein $R_1$ and $R_2$ are independently hydrogen, $R_3$ is $C_{1-23}$ straight or branched or a cyclic alkyl or alkenyl; alkoxyalkyli halogenated alkyl, phenyl, or benzyl alkyl phenyl; $R_4$ and $R_5$ are independently hydrogen or $C_{1-3}$ alkyl; $R_6$ is hydrogen; $R_7$ is benzenesulfonyl or benzoyl optionally substituted by one or more halogens, alkyl groups, amino groups or alkoxy groups; or thiophene carbonyl; and X is oxygen or —NH.

11. A method according to claim 9, wherein $R_1$ and $R_2$, $R_5$, and $R_6$ are hydrogen: $R_3$ is $C_{1-23}$ straight or branched or a cyclic alkyl or alkenyl; alkoxyalkyli halogenated alkyl, phenyl, or benzyl; alkyl phenyl; $R_4$ is methyl; and $R_7$ is benzenesulfonyl or benzoyl optionally substituted by one or more halogens, alkyl groups, amino groups or alkoxy groups; or thiophene carbonyl; and X is oxygen or —NH.

12. A method according to claim 9 wherein the compound is applied to the crop at a dosage rated of from 0.1 to 5 kg/ha.

13. A method according to claim 9 wherein the compound is applied to the crop at a dosage rate of 0.2 to 2 kg/ha.

14. A method for protecting cereals against powdery mildew, by applying to cereal plant or its locus a composition containing an effective amount of a compound having the formula (I)

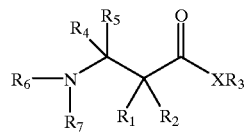

wherein,
a) $R_1$ and $R_2$ are independently hydrogen, $C_{1-8}$ alkyl, phenyl, and phenyl $C_{1-4}$ alkyl
b) $R_3$ is $C_{1-23}$ straight or branched or a cyclic alkyl or alkenyl; alkoxyalkyl halogenated alkyl, phenyl, or benzyl; alkyl phenyl;
c) $R_4$ and $R_5$ are independently hydrogen or $C_{1-8}$ alkyl;
d) $R_6$ is hydrogen; $C_{1-8}$ alkyl; $C_{2-8}$ alkanoyl; phenyl $C_{1-4}$ alkyl, benzoyol wherein the phenyl moiety is optionally substituted by one or more halogen atoms or alkyl groups $C_{2-8}$ alkoxycarbonyl; $CONHR_8$ wherein $R_8$ is hydrogen, $C_{1-8}$ alkyl phenyl, phenyl $C_{1-4}$ alkyl; phenyl $C_{2-4}$ alkyloxycarbonyl;
e) $R_7$ is benzenesulfonyl or benzoyl optionally substituted by one or more halogens, alkyl groups, amino groups or alkoxy groups; or thiophene carbonyl;
f) X is O or NH and salts thereof; and the crop is selected from tomatoes, potatoes and cereals.

15. A method according to claim 14, wherein $R_1$ and $R_2$ are independently hydrogen, $R_3$ is $C_{1-23}$ straight or branched or a cyclic alkyl or alkenyl; alkoxyalkyli halogenated alkyl, phenyl, or benzyl; alkyl phenyl; $R_4$ and $R_5$ are independently hydrogen or $C_{1-3}$ alkyl; $R_6$ is hydrogen: $R_7$ is benzenesulfonyl or benzoyl optionally substituted by one or more halogens, alkyl groups, amino groups or alkoxy groups; or thiophene carbonyl; and X is oxygen or —NH.

16. A method according to claim 14, wherein $R_1$, $R_2$, $R_5$, and $R_6$ are hydrogen: $R_3$ is $C_{1-23}$ straight or branched or a cyclic all or alkenyl; alkoxyalkyli halogenated alkyl, phenyl, or benzyl; alkyl phenyl, or benzyl: $R_4$ is methyl: and $R_7$ is benzenesulfonyl or benzoyl optionally substituted by one or more halogens, alkyl groups, amino groups or alkoxy groups; or thiophene carbonyl; and X is oxygen or NH.

17. A method according to claim 14 wherein the compound is applied post-emergence.

18. A method according to claim 14 wherein the compound is applied to the crop at a dosage rated of from 0.1 to 5 kg/ha.

19. A method for protecting cucumber against downy mildew, by applying to cucumber plant or its locus a composition containing an effective amount of a compound having the formula (I)

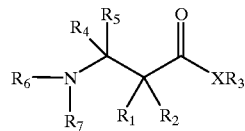

wherein:
a) $R_1$ and $R_2$ are independently hydrogen, $C_{1-4}$ alkyl, phenyl, and phenyl $C_{1-4}$ alkyl
b) $R_3$ is $C_{1-23}$ straight or branched or a cyclic alkyl or alkenyl; alkoxyalkyl halogenated alkyl, phenyl, or benzyl; alkyl phenyl;
c) $R_4$ and $R_5$ are independently hydrogen or $C_{1-8}$ alkyl;
d) $R_6$ is hydrogen; $C_{1-8}$ alkyl; $C_{2-8}$ alkanoyl; phenyl $C_{1-4}$ alkyl, benzoyol wherein the phenyl moiety is optionally substituted by one or more halogen atoms or alkyl groups $C_{2-8}$ alkoxycarbonyl; $CONHR_8$ wherein $R_8$ is hydrogen, $C_{1-8}$ alkyl, phenyl, phenyl $C_{1-4}$ alkyl; phenyl $C_{2-4}$ alkyloxycarbonyl;
e) $R_7$ is benzenesulfonyl or benzoyl optionally substituted by one or more halogens, alkyl groups, amino groups or alkoxy groups; or thiophene carbonyl;
f) X is O or NH and salts thereof; and the crop is selected from tomatoes, potatoes and cereals.

20. A method according to claim 19, wherein $R_1$ and $R_2$ are independently hydrogen, $R_3$ is $C_{1-23}$ straight or branched or a cyclic alkyl or alkenyl; alkoxyalkyli halogenated alkyl, phenyl, or benzyl alkyl phenyl; $R_4$ and $R_5$ are independently hydrogen or $C_{1-3}$ alkyl; $R_6$ is hydrogen; $R_7$ is benzenesulfonyl or benzoyl optionally substituted by one or more halogens, alkyl groups, amino groups or alkoxy groups; or thiophene carbonyl; and X is oxygen or —NH.

21. A method according to claim 19, wherein $R_1$ and $R_2$, R5, and $R_6$ are hydrogen: $R_3$ is $C_{1-23}$ straight or branched or a cyclic alkyl or alkenyl; alkoxyalkyli halogenated alkyl, phenyl, or benzyl; alkyl phenyl; $R_4$ is methyl; and $R_7$ is benzenesulfonyl or benzoyl optionally substituted by one or more halogens, alkyl groups, amino groups or alkoxy groups; or thiophene carbonyl and X is oxygen or —NH.

22. A method according to claim 19 wherein the compound is applied to the crop at a dosage rated of from 0.1 to 5 kg/ha.

23. A method according to claim 19 wherein the compound is applied to the crop at a dosage rate of 0.2 to 2 kg/ha.

24. A method for protecting grapes against downy mildew, by applying to grape plant or its locus a composition containing an effective amount of a compound having the formula (I)

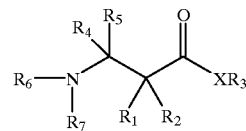

wherein:
a) $R_1$ and $R_2$ are independently hydrogen, $C_{1-8}$ alkyl, phenyl, and phenyl $C_{1-4}$ alkyl
b) $R_3$ is $C_{1-23}$ straight or branched or a cyclic alkyl or alkenyl; alkoxyalkyl halogenated alkyl, phenyl, or benzyl; alkyl phenyl;
c) $R_4$ and $R_5$ are independently hydrogen or $C_{1-8}$ alkyl;
d) $R_6$ is hydrogen; $C_{1-8}$ alkyl; $C_{2-8}$ alkyl; phenyl $C_{1-4}$ alkyl benzoyol wherein the phenyl moiety is optionally substituted by one or more halogen atoms or alkyl groups $C_{2-8}$ alkoxycarbonyl; $CONHR_8$ wherein $R_8$ is hydrogen, $C_{1-8}$ alkyl, phenyl, phenyl $C_{1-4}$ alkyl; phenyl $C_{2-4}$ alkyloxycarbonyl;
e) $R_7$ is benzenesulfonyl or benzoyl optionally substituted by one or more halogens, alkyl groups, amino groups or alkoxy groups; or thiophene carbonyl;
f) X is O or NH and salts thereof.

25. A method according to claim 24, wherein $R_1$ and $R_2$ are independently hydrogen, $R_3$ is $C_{1-23}$ straight or branched or a cyclic alkyl or alkenyl; alkoxyalkyli halogenated alkyl, phenyl, or benzyl alkyl phenyl; $R_4$ and $R_5$ are independently hydrogen or $C_{1-3}$ alkyl; & is hydrogen; $R_7$ is benzenesulfonyl or benzoyl optionally substituted by one or more halogens, alkyl groups, amino groups or alkoxy groups; or thiophene carbonyl; and X is oxygen or —NH.

26. A method according to claim 24, wherein $R_1$ and $R_7$ $R_5$, and Pd are hydrogen: $R_3$ is $C_{1-23}$ straight or branched or a cyclic alkyl or alkenyl; alkoxyalkyli halogenated alkyl, phenyl, or benzoyl; alkyl phenyl; R4 is methyl; and $R_7$ is benzenesulfonyl or benzoyl optionally substituted by one or more halogens, alkyl groups, amino groups or alkoxy groups; or thiophene carbonyl; and X is oxygen or —NH.

27. A method according to claim 24 wherein the compound is applied to the crop at a dosage rated of from 0.1 to 5 kg/ha.

28. A method according to claim 24 wherein the compound is applied to the crop 250 at a dosage rate of 0.2 to 2 kg/ha.

29. A method for protecting melons against downy mildew, by applying to melon plant or its locus a composition containing an effective amount of a compound having the formula (I)

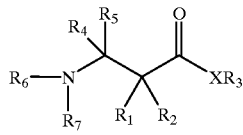

wherein:
a) $R_1$ and $R_2$ are independently hydrogen, $C_{1-8}$ alkyl, phenyl, and phenyl $C_{1-4}$ alkyl
b) $R_3$ is $C_{1-23}$ straight or branched or a cyclic alkyl or alkenyl; alkoxyalkyl halogenated alkyl phenyl, or benzyl; alkyl phenyl;
c) $R_4$ and $R_5$ are independently hydrogen or $C_{1-8}$ alkyl;
d) $R_6$ is hydrogen; $C_{1-8}$ alkyl; $C_{2-8}$ alkanoyl; phenyl $C_{1-4}$ alkyl, benzoyol wherein the phenyl moiety is optionally substituted by one or more halogen atoms or alkyl groups $C_{2-8}$ alkoxycarbonyl; $CONHR_8$ wherein $R_8$ is hydrogen, $C_{1-8}$ alkyl, phenyl, phenyl $C_{1-4}$ alkyl; phenyl $C_{2-4}$ alkyloxycarbonyl;
e) $R_7$ is benzenesulfonyl or benzoyl optionally substituted by one or more halogens, alkyl groups, amino groups or alkoxy groups; or thiophene carbonyl;
f) X is O or NH and salts thereof.

30. A method according to claim 24, wherein $R_1$ and $R_2$ are independently hydrogen; $R_3$ is $C_{1-23}$ straight or branched or a cyclic alkyl or alkenyl; alkoxyalkyli halogenated alkyl phenyl, or benzyl alkyl phenyl; $R_4$ and $R_5$ are independently hydrogen or $C_{1-3}$ alkyl; $R_6$ is hydrogen; $R_7$ is benzenesulfonyl or benzoyl optionally substituted by one or more halogens, alkyl groups, amino groups or alkoxy groups; or thiophene carbonyl; and X is oxygen or —NH.

31. A method according to claim 24, wherein $R_1$ and $R_2$, R5, and $R_6$ are hydrogen: $R_3$ is $C_{1-23}$ straight or branched or a cyclic alkyl or alkenyl; alkoxyalkyli; halogenated alkyl, phenyl, or benzyl; alkyl phenyl; R4 is methyl; and $R_7$ is benzenesulfonyl or benzoyl optionally substituted by one or more halogens, alkyl groups, amino groups or alkoxy groups; or thiophene carbonyl; and X is oxygen or —NH.

32. A method according to claim 29 wherein the compound is applied to the crop at a dosage rated of from 0.1 to 5 kg/ha.

33. A method according to claim 29 wherein the compound is applied to the crop at a dosage rate of 0.2 to 2 kg/ha.

34. A method according to claim 4, wherein the compound is applied to the plant leaves or stems, the plant roots, the soil, or the seeds, tubers or bulbs of the plant.

35. A method according to claim 4, wherein the compound is applied pre-emergent or post-emergent.

36. A method according to claim 9, wherein the compound is applied to the plant leaves or stems, the plant roots, the soil, or the seeds, tubers or bulbs of the plant.

37. A method according to claim 9, wherein the compound is applied pre-emergent or post-emergent.

38. A method according to claim 14, wherein the compound is applied to the plant leaves or stems, the plant roots, the soil, or the seeds, tubers or bulbs of the plant.

39. A method according to claim 14, wherein the compound is applied pre-emergent or post-emergent.

40. A method according to claim 19, wherein the compound is applied to the plant leaves or stems, the plant roots, the soil, or the seeds, tubers or bulbs of the plant.

41. A method according to claim 19, wherein the compound is applied pre-emergent or post-emergent.

42. A method according to claim 24, wherein the compound is applied to the plant leaves or stems, the plant roots, the soil, or the seeds, tubers or bulbs of the plant.

43. A method according to claim 24, wherein the compound is applied pre-emergent or post-emergent.

44. A method according to claim 29, wherein the compound is applied to the plant leaves or stems, the plant roots, the soil, or the seeds, tubers or bulbs of the plant.

45. A method according to claim 29, wherein the compound is applied pre-emergent or post-emergent.

46. A compound according to claim 1, wherein the compound is selected from the group consisting of D,L-N-benzensulfonyl-3-amino N-benzyl butyramide; D,L-N-benzensulfonyl-3-aminobutyranilide; D,L-N-β-chlorobenzoyl-3-aminobutyric acid-2-chloroethyl ester; D,L-N-β-methyl benzoyl-3-aminobutyric acid, n-octyl ester; N-β-methyl benzoyl-3-aminobutyric acid, sec. butyl ester; D,L-N-3,4,-dichlorobenzoyl-3-aminobutyric acid, n-octyl ester; DL-N-benzoyl-3-aminobutyric acid-2-chloroethyl ester; N-β-methyl benzoyl-3-aminobutyric acid-1-methyl-1-pentyl ester; DL-N-benzene sulfonyl-3-aminobutyric acid, n-octyl ester; N-benzene sulfonyl-3-aminobutyric acid, sec butyl ester; N-benzene sulfonyl-3-aminobutyric acid, 1-methyl-1-butyl ester; D,L N-4-methoxybenzoyl-3-aminobutyric acid heptyl ester; D,L N-3,5-dimethylbezoyl-3-aminobutyric acid heptyl ester; D,L N-2,6-difluorobenzoyl-3-aminobutyric acid heptyl ester; D,L N-4-tertbutylbenzoyl-3-aminobutyric acid heptyl ester; D,L N-4-methylbenzenesulfonyl-3-aminobutyric acid 1-methylpentyl ester; D,L N-benzenesulfonyl-3-aminbutyric acid 3-phenylpropyl ester; D,L N-4-cholrobenzoyl-3-aminobutyric acid 1-methylpentyl ester; D,L N-benzenesulfonyl-3-aminobutyric acid 2-(trichloromethyl) ethyl ester; D,L N-4-methylbenzenesulfonyl-3-aminobutyric 1-methylpropyll ester; D,L N-3,4-dimethylbezoyl-3-aminobutyric acid 1-methylbutyl ester; D,L N-3-methylbezoyl-3-aminobutyric acid heptyl ester; D,L N-3,5-dimethylbezoyl-3-aminobutyric acid 1-methylpentyl ester; D,L N-2,6-dichlorobenzoyl-3-aminobutyric acid heptyl ester; D,L N-2,6-dichlorobenzoyl-3-aminobutyric acid 1-methylpentyl ester; D,L N-4-methylbenzoyl-3-aminobutyric acid 3-phenylpropyl ester; D,L N-3,5-dimethylbezoyl-3-aminobutyric acid 2-chloroethyl ester; D,L N-4-methoxybenzoyl-3-aminobutyric acid 2-chloroethyl ester; D,L N-benzoyl-3-aminobutyric acid 2-(tricholoromethyl) ethyl ester; D,L N-4-chlorobenzoyl-3-aminobutyric acid heptyl ester; D,L N-benzenesulfonyl-3-aminobutyric acid 1-methyl- 2-methoxyethyl ester; D,L N-2-methylbezoyl-3-aminobutyric acid heptyl ester; D,L N-4- methylbenzenesulfonyl-3-aminobutyric acid 2-bromoethyl ester; D,L N-4-methylbenzenesulfonyl-3-aminobutyric acid heptyl ester; D,L N-4-chlorobenzenesulfonyl-3-aminobutyric acid propyl ester; D,L N-4-methylbenzoyl-3-aminobutyric acid 2-(trichloromethyl)ether ester; D,L N-4-methylbenzoyl-3-aminobutyric acid cyclohexyl ester; D,L-N-benzoyl-3-aminobutyric acid cyclohexyl ester; D,L N-benzenesulfonyl-3-aminobutyric acid cyclohexyl ester; D,L N-4-chlorobenzenesulfonyl-3-aminobutyric acid heptyl ester; 44 D,L N-benzenesulfonyl-3-aminobutyric acid propyl ester; D,L N-benzoyl-3-aminobutyric acid 2-propenyl ester; D,L N-4-methylbenzoyl-3-aminobutyric acid 1-methylhexyl ester; D,L N-4-methylbenzoyl-3-aminobutyric acid 1-methyldecanyl ester; D,L N-3,4-dimethylbezoyl-3-aminobutyric acid heptyl ester; D,L N-4-methylbezoyl-3-aminobutyric acid 1-methylpentyl ester; D,L N-2-methylaminobenzoyl-3-aminobutyric acid methyl ester; D,L N-4-chlorobenzensulfonyl-3-aminobutyric acid 1-methylpentyl ester; D,L N-benzensulphonyl-3-aminobutyric acid 3-phenylpropyl ester; D,L N-2-methylaminobenzoyl-3-aminobutyric acid 1-methylpentyl ester; D,L N-benzensulfonyl-3-aminobutyric acid 3,5-dichlorophenyl; D,L N-4-methylaminobenzoyl-3-aminobutyric acid 1-methylpentyl ester; D,L N-3,4-dimethylbenzoyl-3-aminobutyric acid octyl ester; D,L, N-2-thiophenecarbonyl-3-aminobutyric acid octyl ester; and D,L N-2-thiophenecarbonyl-3-aminobutyric acid 1-methylpentyl ester.

47. A compound according to claim 4, wherein the compound is selected from the group consisting of D,L-N-benzensulfonyl- 3-amino N-benzyl butyramide; D,L-N-benzensulfonyl-3-aminobutyranilide; D,L-N-β-chlorobenzoyl-3-aminobutyric acid-2-chloroethyl ester; D,L-N-β-methyl benzoyl-3-aminobutyric acid, n-octyl ester; N-β-methyl benzoyl-3-aminobutyric acid, sec. butyl ester; D,L-N-3,4,-dichlorobenzoyl-3-aminobutyric acid, n-octyl ester; DL-N-benzoyl-3-aminobutyric acid-2-chloroethyl ester; N-β-methyl benzoyl-3-aminobutyric acid-1-methyl-1-pentyl ester; DL-N-benzene sulfonyl-3-aminobutyric acid, n-octyl ester; N-benzene sulfonyl-3-aminobutyric acid, sec butyl ester; N-benzene sulfonyl-3-aminobutyric acid, 1-methyl-1-butyl ester; D,L N-4-methoxybenzoyl-3-aminobutyric acid heptyl ester; D,L N-3,5-dimethylbezoyl-3-aminobutyric acid heptyl ester; D,L N-2,5-difluorobenzoyl-3-aminobutyric acid heptyl ester; D,L N-4-tertbutylbenzoyl-3-aminobutyric acid heptyl ester; D,L N-4-methylbenzenesulfonyl-3-aminobutyric acid 1-methylpentyl ester; D,L N-benzenesulfonyl-3-aminbutyric acid 3-phenylpropyl ester; D,L N-4-cholrobenzoyl-3-aminobutyric acid 1-methylpentyl ester; D,L N-benzenesulfonyl-3-aminobutyric acid 2-(trichoromethyl) ethyl ester; D,L N-4-methylbenzenesulfonyl-3-aminobutyric 1-methylpropyll ester; D,L N-3,4-dimethylbezoyl-3-aminobutyric acid 1-methylbutyl ester; D,L N-3-methylbezoyl-3-aminobutyric acid heptyl ester; D,L N-3,5-dimethylbezoyl-3-aminobutyric acid 1-methylpentyl ester; D,L N-2,6-dichlorobenzoyl-3-aminobutyric acid heptyl ester; D,L N-2,6-dichlorobenzoyl-3-aminobutyric acid 1-methylpentyl ester; D,L N-4-methylbenzoyl-3-aminobutyric acid 3-phenylpropyl ester; D,L N-3,5-dimethylbezoyl-3-aminobutyric acid 2-chloroethyl ester; D,L N-4-methoxybenzoyl-3-aminobutryic acid 2-chloroethyl ester; D,L N-benzoyl-3-aminobutyric acid 2-(tricholoromethyl) ethyl ester; D,L N-4-chlorobenzoyl-3-aminobutyric acid heptyl ester; D,L N-benzenesulfonyl-3-aminobutyric acid 1-methyl-2-methoxyethyl ester; D,L N-2-methylbezoyl-3-aminobutyric acid heptyl ester; D,L N-4-methylbenzenesulfonyl-3-aminobutyric acid 2-bromoethyl ester; D,L N-4-methylbenzenesulfonyl-3-aminobutyric acid heptyl ester; D,L N-4-chlorobenzenesulfonyl-3-aminobutyric acid propyl ester; D,L N-4-methylbenzoyl-3-aminobutyric acid 2-(trichloromethyl)ether ester; D,L N-4-methylbenzoyl-3-aminobutyric acid cyclohexyl ester; D,L-N-benzoyl-3-aminobutyric acid cyclohexyl ester; D,L N-benzenesulfonyl-3-aminobutyric acid cyclohexyl ester; D,L N-4-chlorobenzenesulfonyl-3-aminobutyric acid heptyl ester; 44 D,L N— benzenesulfonyl-3-aminobutyric acid propyl ester; D,L N-benzoyl-3-aminobutyric acid 2-propenyl ester; D,L N-4-methylbenzoyl-3-aminobutyric acid 1-methylhexyl ester; D,L N-4-methylbenzoyl-3-aminobutyric acid 1-methyldecanyl ester; D,L N-3,4-dimethylbezoyl-3-aminobutyric acid heptyl ester; D,L N-4-methylbezoyl-3-aminobutyric acid 1-methylpentyl ester; D,L N-2-methylaminobenzoyl-3-aminobutyric acid methyl ester; D,L N-4-chlorobenzensulfonyl-3-aminobutyric acid 1-methylpentyl ester; D,L N-benzensulphonyl-3-aminobutyric acid 3-phenylpropyl ester; D,L N-2-methylaminobenzoyl-3-aminobutyric acid 1-methylpentyl ester; D,L N-benzensulfonyl-3-aminobutyric acid 3,5-dichlorophenyl; D,L N-4-methylaminobenzoyl-3-aminobutyric acid 1-methylpentyl ester; D,L N-3,4-dimethylbenzoyl-3-aminobutyric acid octyl ester; D,L, N-2-thiophenecarbonyl-3-aminobutyric acid octyl ester; and D,L N-2-thiophenecarbonyl-3-aminobutyric acid 1-methylpentyl ester.

48. A compound according to claim 9, wherein the compound is selected from the group consisting of D,L-N-benzensulfonyl-3-amino N-benzyl butyramide; D,L-N-benzensulfonyl-3-aminobutyranilide; D,L-N-β-chlorobenzoyl-3-aminobutyric acid-2-chloroethyl ester; D,L-N-β-methyl benzoyl-3-aminobutyric acid, n-octyl ester; N-β-methyl benzoyl-3-aminobutyric acid, sec. butyl ester; D,L-N-3,4,-dichlorobenzoyl-3-aminobutyric acid, n-octyl ester; DL-N-benzoyl-3-aminobutyric acid-2-chloroethyl ester; N-β-methyl benzoyl-3-aminobutyric acid-1-methyl-1-pentyl ester; DL-N-benzene sulfonyl-3-aminobutyric acid, n-octyl ester; N-benzene sulfonyl-3-aminobutyric acid, sec butyl ester; N-benzene sulfonyl-3-aminobutyric acid, 1-methyl-1-butyl ester; D,L N-4-methoxybenzoyl-3-aminobutyric acid heptyl ester; D,L N-3,5-dimethylbezoyl-3-aminobutyric acid heptyl ester; D,L N-2,6-difluorobenzoyl-3-aminobutyric acid heptyl ester; D,L N-4-tertbutylbenzoyl-3-aminobutyric acid heptyl ester; D,L N-4-methylbenzenesulfonyl-3-aminobutyric acid 1-methylpentyl ester; D,L N-benzenesulfonyl-3-aminbutyric acid 3-phenylpropyl ester; D,L N-4-cholrobenzoyl-3-aminobutyric acid 1-methylpentyl ester; D,L N-benzenesulfonyl-3-aminobutyric acid 2-(trichloromethyl) ethyl ester; D,L N-4-methylbenzenesulfonyl-3-aminobutyric 1-methylpropyll ester; D,L N-3,4-dimethylbezoyl-3-aminobutyric acid 1-methylbutyl ester; D,L N-3-methylbezoyl-3-aminobutyric acid heptyl ester; D,L N-4-chlorobenzenesulfonyl-3-aminobutyric acid propyl ester; D,L N-4-methylbenzoyl-3-aminobutyric acid 2 -(trichloromethyl)ether ester; D,L N-4-methylbenzoyl-3-aminobutyric acid cyclohexyl ester; D,L-N-benzoyl-3-aminobutyric acid cyclohexyl ester; D,L N-benzenesulfonyl-3-aminobutyric acid cyclohexyl ester; D,L, N-2-thiophenecarbonyl-3-aminobutyric acid octyl ester; D,L N-2-thiophenecarbonyl-3-aminobutyric acid 1-methylpentyl ester; D,L N-2-methylaminobenzoyl-3-aminobutyric acid 1-methylpentyl ester; D,L N-benzenesulfonyl-3-aminobutyric acid 3-phenylpropyl ester; and D,L N-4-chlorobenzenesulfoyl-3-aminobutyric acid 1-methylpentyl ester.

49. A compound according to claim 14, wherein the compound is selected from the group consisting of D,L-N-benzensulfonyl-3-amino N-benzyl butyramide; D,L-N-benzensulfonyl-3-aminobutyranilide; D,L-N-β-chlorobenzoyl-3-aminobutyric acid-2-chloroethyl ester; D,L-N-β-methyl benzoyl-3-aminobutyric acid, n-octyl ester; N-β-methyl benzoyl-3-aminobutyric acid, sec. butyl ester; D,L-N-3,4,-dichlorobenzoyl-3-aminobutyric acid, n-octyl ester; DL-N-benzoyl-3-aminobutyric acid-2-chloroethyl ester; N-β-methyl benzoyl-3-aminobutyric acid-1-methyl-1-pentyl ester; DL-N-benzene sulfonyl-3-aminobutyric acid, n-octyl ester; N-benzene sulfonyl-3-aminobutyric acid, sec butyl ester; N-benzene sulfonyl-3-aminobutyric acid, 1-methyl-1-butyl ester; D,L N-4-methoxybenzoyl-3-aminobutyric acid heptyl ester; D,L N-3,5-dimethylbezoyl-3-aminobutyric acid heptyl ester; D,L N-4-tertbutylbenzoyl-3-aminobutyric acid heptyl ester; D,L N-4-methylbenzenesulfonyl-3-aminobutyric acid 1-methylpentyl ester; D,L N-2-methylbezoyl-3-aminobutyric acid heptyl ester; D,L N-4-chlorobenzenesulfonyl-3-aminobutyric acid propyl ester; D,L-N-benzoyl- 3-aminobutyric acid cyclohexyl ester; D,L N-benzenesulfonyl-3-aminobutyric acid cyclohexyl ester; D,L N-benzoyl-3-aminobutyric acid 2-propenyl ester; D,L N-4-methylbenzoyl-3-aminobutyric acid 1-methylhexyl ester; D,L N-4-methylbenzoyl-3-amionbutyric acid 1-methyldecanyl ester; D,L N-3,4-dimethylbezoyl-3-aminobutyric acid heptyl ester; D,L N-2-methylaminobenzoyl-3-aminobutyric acid methyl ester; D,L N-2-methylaminobenzoyl-3-aminonutyric acid methyl ester; D,L N-4-methylbezoyl-3-aminobutyric acid 1-methylpentyl ester; D,L N-4-chlorobenzensulfonyl-3-aminobutyric acid 1-methylpentyl ester; D,L N-2-methylaminobenzoyl-3-aminobutyric acid methyl ester; D,L N-3,4-dimethylbenzoyl-3-aminobutyric acid octyl ester; and D,L N-benzensulfonyl-3-aminobutyric acid 3,5-dichlorophenyl.

50. A compound according to claim 19, wherein the compound is selected from the group consisting of D,L N-4-chlorobenzenesulfonyl-3-aminobutyric acid propyl ester; D,L N-4-methylbenzoyl-3-aminobutyric acid 2-(trichloromethyl)ether ester; D,L N-4-methylbenzoyl-3-aminobutyric acid cyclohexyl ester; D,L-N-benzoyl-3-aminobutyric acid cyclohexyl ester; D,L N-benzenesulfonyl-3-aminobutyric acid cyclohexyl ester; D,L N-4-chlorobenzenesulfonyl-3-aminobutyric acid heptyl ester; and D,L N-2-methylaminobenzoyl-3-aminobutyric acid 1-methylpentyl ester.

51. A compound according to claim 24, wherein the compound is selected from the group consisting of D,L N-2,6-difluorobenzoyl-3-aminobutyric acid heptyl ester; D,L N-4-tertbutylbenzoyl-3-aminobutyric acid heptyl ester; D,L N-4-methylbenzenesulfonyl-3-aminobutyric acid 1-methylpentyl ester; D,L N-benzenesulfonyl-3-aminbutyric acid 3-phenylpropyl ester; D,L N-4-cholrobenzoyl-3-aminobutyric acid 1-methylpentyl ester; D,L N-benzenesulfonyl-3-aminobutyric acid 2-(trichloromethyl)ethyl ester; D,L N-4-methylbenzenesulfonyl-3-aminobutyric 1-methylpropyll ester; D,L N-3,5-dimethylbezoyl-3-aminobutyric acid 1-methylpentyl ester; D,L N-2,6-dichlorobenzoyl-3-aminobutyric acid heptyl ester; D,L N-2,6-dichlorobenzoyl-3-aminobutyric acid 1-methylpentyl ester; D,L N-4-methylbenzoyl-3-aminobutyric acid 3-phenylpropyl ester; D,L N-3,5-dimethylbezoyl-3-aminobutyric acid 2-chloroethyl ester; D,L N-4-methoxybenzoyl-3-aminobutryic acid 2-chloroethyl ester; D,L N— benzoyl-3-aminobutyric acid 2-(tricholoromethyl)ethyl ester; D,L N-4-chlorobenzoyl-3-aminobutyric acid heptyl ester; D,L N-benzenesulfonyl-3-aminobutyric acid 1-methyl-2-methoxyethyl ester; and D,L N-benzenesulfonyl-3-aminobutyric acid 3-phenylpropyl ester.

52. A compound according to claim 24, wherein the compound is selected from the group consisting of D,L N-4-methoxybenzoyl-3-aminobutyric acid heptyl ester; D,L N-4-tertbutylbenzoyl-3-aminobutyric acid heptyl ester; D,L N-benzenesulfonyl-3-aminbutyric acid 3-phenylpropyl ester; D,L N-4-cholrobenzoyl-3-aminobutyric acid 1-methylpentyl ester; D,L N-benzenesulfonyl-3-aminobutyric acid 2-(trichloromethyl)ethyl ester; D,L N-3-methylbezoyl-3-aminobutyric acid heptyl ester; D,L N-3,5-dimethylbezoyl-3-aminobutyric acid 1-methylpentyl ester; D,L N-2,6-dichlorobenzoyl-3-aminobutyric acid 1-methylpentyl ester; D,L N-3,5-dimethylbezoyl-3-aminobutyric acid 2-chloroethyl ester; D,L N-benzoyl-3-aminobutyric acid 2-(tricholoromethyl)ethyl ester; D,L N-2-methylbezoyl-3-aminobutyric acid heptyl ester; D,L N-4-methylbenzenesulfonyl-3-aminobutyric acid 2-bromoethyl ester; D,L N-4-methylbenzenesulfonyl-3-aminobutyric acid heptyl ester; and D,L N-benzenesulfonyl-3-aminobutyric acid 3-phenylpropyl ester.

* * * * *

UNITED STATES PATENT AND TRADEMARK OFFICE
CERTIFICATE OF CORRECTION

PATENT NO.   : 6,348,614 B1
DATED        : February 19, 2002
INVENTOR(S)  : Cohen et al.

It is certified that error appears in the above-identified patent and that said Letters Patent is hereby corrected as shown below:

<u>Title page,</u>
Item [75], Inventors, delete "Yogal" and insert therefor -- Yigal --.

Signed and Sealed this

Eighteenth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,348,614 B1
DATED         : February 19, 2002
INVENTOR(S)   : Cohen et al.

Page 1 of 1

It is certified that error appears in the above-identified patent and that said Letters Patent is hereby corrected as shown below:

<u>Column 21, line 29; Column 22, line 30; Column 23, lines 53 and 28,</u>
Delete "compound" and insert therefor -- method. --.

Signed and Sealed this

Second Day of September, 2003

JAMES E. ROGAN
*Director of the United States Patent and Trademark Office*